(12) United States Patent
Swinkels et al.

(10) Patent No.: US 10,422,805 B2
(45) Date of Patent: Sep. 24, 2019

(54) RELEASE REAGENT FOR VITAMIN D

(75) Inventors: Leon Maria Jacobus Wilhelmus Swinkels, Bemmel (NL); Antonius Franciscus Maas, Grave (NL); Michael Franciscus Wilhelmus Cornelis Martens, Helmond (NL)

(73) Assignee: FUTURE DIAGNOSTICS B.V., Wijchen (NL)

(*) Notice: Subject to any disclaimer, the term of this patent is extended or adjusted under 35 U.S.C. 154(b) by 242 days.

(21) Appl. No.: 13/993,285

(22) PCT Filed: Dec. 27, 2011

(86) PCT No.: PCT/NL2011/050905
§ 371 (c)(1),
(2), (4) Date: Nov. 21, 2013

(87) PCT Pub. No.: WO2012/091569
PCT Pub. Date: Jul. 5, 2012

(65) Prior Publication Data
US 2014/0147935 A1    May 29, 2014

(30) Foreign Application Priority Data

Dec. 28, 2010  (EP) .................................. 10197208
Jun. 9, 2011   (EP) .................................. 11169314

(51) Int. Cl.
    G01N 33/82    (2006.01)
(52) U.S. Cl.
    CPC .................................. *G01N 33/82* (2013.01)
(58) Field of Classification Search
    None
    See application file for complete search history.

(56) References Cited

U.S. PATENT DOCUMENTS

| 4,452,903 A * | 6/1984 | Lee et al. ...................... 436/540 |
| 5,981,779 A | 11/1999 | Holick et al. |
| 7,087,395 B1 * | 8/2006 | Garrity .................. G01N 33/82 422/417 |
| 7,482,162 B2 * | 1/2009 | Laurie et al. .................. 436/20 |
| 2004/0132104 A1 | 7/2004 | Sackrison et al. |

FOREIGN PATENT DOCUMENTS

| JP | 2000-503641 A1 | 3/2000 |
| WO | 97/24127 A1 | 7/1997 |
| WO | 0246746 A2 | 6/2002 |
| WO | 02057797 A2 | 7/2002 |
| WO | 03023391 A2 | 3/2003 |
| WO | 2007039194 A1 | 4/2007 |
| WO | 2007140962 A2 | 12/2007 |
| WO | WO 2008092917 A1 * | 8/2008 |
| WO | 2011122948 A1 | 10/2011 |

OTHER PUBLICATIONS

Jarvis et al., "Surface Chemistry of Fluorochemicals." U.S. Naval Research Laboratory, Surface Chemistry Branch Chemistry Division, (NRL Report 6324), (1965), p. 11-32.*
Kadiyala et al., Perfluorooctanoic acid for shotgun proteomics, PLoS One, 5(12), (2010), p. 1-7.*
Sheperd et al., The potential of fluorinated surfactants in membrane biochemistry, Analytical Biochemistry, 224, (1995), p. 21-27.*
Wu, et al, Interaction of perfluorooctanoic acid with human serum albumin, BMC Structural Biology, May 14, 2009, 8 pages.
Zhang, et al, Binding of PFOS to serum albumin and DNA: insight into the molecular toxicity of perfluorochennicals, BMC Molecular Biology, published Feb. 25, 2009, 12 pages.
Parsons, Ravis and Clark, Binding of warfarin by human albumin in the presence of a periluorochemical blood substitute, Archives Internationales De Pharmacodynamie Et De Therapie, France, 1985, vol. 277, No. 1:4-14.

* cited by examiner

*Primary Examiner* — Bao Thuy L Nguyen
*Assistant Examiner* — Ellen J Marcsisin
(74) *Attorney, Agent, or Firm* — Patterson Intellectual Property Law, P.C.; Seth R. Ogden

(57) ABSTRACT

Disclosed is an invention in the field of conducting an immunoassay of 25(OH) vitamin D in blood or blood components, notably serum or plasma. The invention employs a perfluoro alkyl acid, or a salt thereof, to release 25(OH) vitamin D from vitamin D binding protein. Thereafter the binding protein comprising the 25-OH vitamin D is subjected to a competitive binding assay with a labeled vitamin D compound.

6 Claims, 2 Drawing Sheets

RELEASE REAGENT FOR VITAMIN D

FIELD OF THE INVENTION

The present invention pertains to an immunoassay method, including point-of-care tests, for assaying a sample of blood or blood components for total vitamin D or Vitamin D metabolites, in particular 25-hydroxy vitamin D using an agent to release Vitamin D from endogenous binding proteins.

BACKGROUND OF THE INVENTION

The substances referred to as "vitamin D" encompass a group of fat-soluble prohormones, as well as metabolites and analogues thereof. The main forms in which vitamin D occurs in the body are vitamin $D_2$ (ergocalciferol) and vitamin $D_3$ (cholecalciferol). The latter is the endogenous form of vitamin D, which humans can form in the skin under the influence of sunlight. The former is an exogenous form of vitamin D, taken up with food. In the US, Vitamin D2 is used as the pharmaceutical vitamin D supplement.

Whilst vitamin $D_2$ and $D_3$ differ in the molecular structure of their side-chains, they share the same biological activity in being prohormones, metabolized in two steps to, ultimately, 1,25 dihydroxy vitamin D (calcitriol, or 1,25 dihydroxy cholecalciferol). The preceding metabolite, 25-hydroxy vitamin D or calcidiol, results from conversion in the liver, and is considered the storage form of vitamin D in the body.

Circulating vitamin D consists mainly of 25(OH)vitamin D3 and 25(OH)vitamin D2. Biologically, 25(OH)vitamin D2 is as effective as 25(OH)vitamin D3. The half-life of 25(OH)vitamin D2 in the circulation is shorter. For clinical practice the use of an 25(OH)vitamin D assay that measures both 25(OH)vitamin D3 as well as 25(OH)vitamin D2 is recommended (1).

Vitamin D has long been recognized as an important substance, the active form of which plays a role in the formation and maintenance of bone, as well as in other processes in the human or animal body. Thus, it serves to increase the concentration of calcium in the bloodstream, by promoting absorption of calcium and phosphorus from food in the intestines, and re-absorption of calcium in the kidneys; enabling normal mineralization of bone and preventing hypocalcemic tetany. It is also necessary for bone growth and bone remodeling by osteoblasts and osteoclasts.

Vitamin D deficiency results in impaired bone mineralization and leads to bone softening diseases, rickets in children and osteomalacia in adults, and possibly contributes to osteoporosis.

In recent years it has been recognized that Vitamin D plays a number of other roles in human health. It can modulate the immune function and reduce inflammation. It has also been suggested that Vitamin D may prevent colon, breast and ovarian cancer.

Thus, it is of the essence for a person's or animal's health to have an adequate level of vitamin D.

Yet, excess of vitamin D (which may occur as a result of overdosing) is toxic. Some symptoms of vitamin D toxicity are hypercalcaemia (an elevated level of calcium in the blood) caused by increased intestinal calcium absorption. Vitamin D toxicity is known to be a cause of high blood pressure. Gastrointestinal symptoms of vitamin D toxicity can include anorexia, nausea, and vomiting. These symptoms are often followed by polyuria (excessive production of urine), polydipsia (increased thirst), weakness, nervousness, pruritus (itch), and eventually renal failure.

Clearly, it is important to be able to diagnose subjects for a possible vitamin D deficiency. It is also important, particularly for subjects that are on vitamin D supplementation, to be able to test subjects for a potential excess of vitamin D. In clinical practice, the serum level of 25-hydroxyvitamin D is considered to be the primary indicator of the vitamin D status. (2).

Almost all circulating 25(OH)-vitamin D in serum is bound by vitamin D binding protein (88%) and Albumin (12%). Vitamin D binding protein (DBP) is an abundant protein, with a concentration of 250-400 mg/L of serum. Vitamin D is bound to DBP with a relatively high affinity, close to that of antibodies ($5*10^8 M^{-1}$).

An accurate measurement of the concentration of Vitamin D in serum requires the release of bound vitamin D from the DBP.

Early methods for the determination of Vitamin D included an extraction step using organic solvents such as acetonitrile. Other approaches have relied on dissociation of Vitamin D-DBP complex using a high or low pH (WO2004/063704). Other methods rely on the competitive displacement of Vitamin D from endogenous binding proteins using ANS (U.S. Pat. No. 7,482,162). Recently methods including proteolytic digestion of DBP have been published (WO 2008/092917 A1). Armbruster has published a method for direct measurement of Vitamin D using displacement by hydroxylated aromatic carboxylic acid (WO 2003/023391). The method described by Kyriatsoulis relies on the release of Vitamin D from Vitamin-D binding protein by using a reagent with a pH from 3.8 to 4.8 and 5-30% DMSO, a liquid organic amide and optionally 0.5-5% of a short chain alcohol. Kobold presented a method for the release based on a salt with a cation having a quaternary nitrogen based ion. EP2007/140962. US 2008/0182341 mentions stabilizing agents and capture ligands for use in assays measuring analyte concentrations. These stabilizing agents are disclosed against the background of certain alkyl amino fluoro surfactants. The inventors suggest that this surfactant facilitates the measurement of free unbound analyte versus bound analyte by stabilizing the equilibrium. Fluorocarbon octanoic acid is mentioned as a potential hazardous substance.

Background references on assaying Vitamin D include Hollis B W. Measuring 25-hydroxyvitamin D in a clinical environment: challenges and needs. Am J Clin Nutr. 2008 August; 88(2):507S-510S; Holick M F. Vitamin D: extraskeletal health. Endocrinol Metab Clin North Am. 2010 June; 39(2):381-400.

SUMMARY OF THE INVENTION

This invention, in one aspect, presents an in vitro method for the qualitative assaying of blood or blood components for the presence of 25-hydroxy vitamin D, comprising:

(a) adding to the sample a perfluoro alkyl acid with a carbon chain length of from 4 to 12 carbon atoms, or a salt thereof, in order to enable the release of Vitamin D from Vitamin D binding protein;

(b) optionally diluting the sample with a diluent;

(c) subjecting the mixture to incubation with an immobilized binding protein, notably an anti-Vitamin D antibody;

(d) contacting the sample with a conjugate of Vitamin D and a functional label that binds to the anti-Vitamin D antibody in a competitive way (e) determining the concentration of labeled vitamin D compound bound to the binding protein In another aspect, the invention resides in a kit for conducting the foregoing method.

In yet another aspect the method can be used for "point-of-care" testing. The latter refers to testing at or near the site of patient care, i.e. rather than drawing blood samples and sending these to a diagnostic laboratory, a sample can be immediately introduced into a portable, preferably handheld device which is able to perform the assay in as limited a number of steps as possible, and with as limited a number of manual operations as possible.

DETAILED DESCRIPTION OF THE INVENTION

Figure 1:
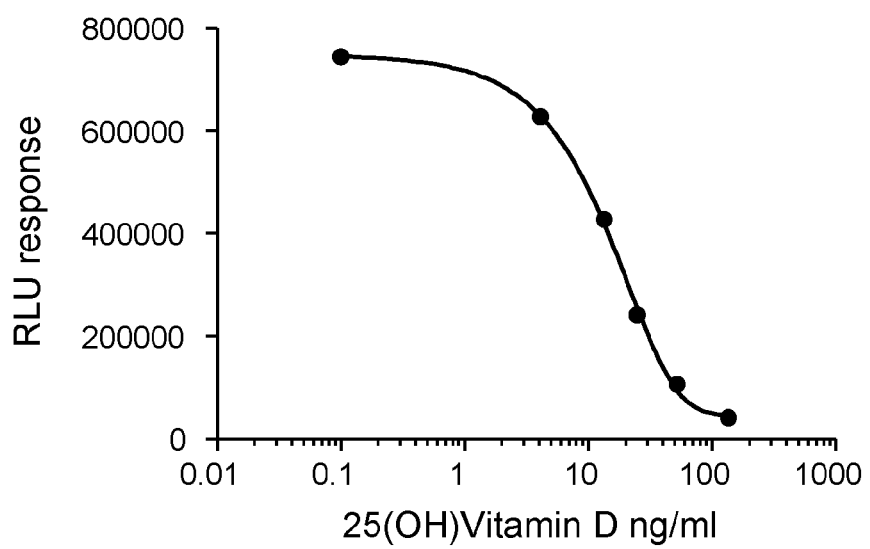
FIG. 1 depicts a 25(OH)Vitamin D calibration curve.

In a broad sense, the invention concerns the determination of Vitamin D in blood or blood components, notably serum or plasma, by an immunoassay using a perfluoroalkyl acid or salt thereof with a carbon chain length of 4 to 12 to release Vitamin D from endogenous binding proteins.

Conceivably, in the invention use can be made of perfluoroalkyl carboxylic acid or perfluoro sulfonic acid or salts thereof. In particular Perfluorhexanoic acid (PFHxA) or perfluoroctanoic acid (PFOA) can be used.

The assay generally involves
(a) adding a diluent/assay buffer to sample
(b) adding magnetic particles coated with anti-vitamin D antibody
(c) incubating the sample for an amount of time
(d) adding a conjugate of vitamin D and a functional label;
(e) determining the amount of the conjugate of vitamin D and the functional label bound to the antibody.

Such samples can be drawn, in any manner known in the art, from a subject, particularly a human, in whose blood it is desired to assay the presence of 25-OH vitamin D.

The sample preferably is diluted with an aqueous diluent. Preferably the diluent is an assay buffer. The dilution can take place before, during, or after the addition of the antibody. The sample diluent or assay buffer can be aqueous-based, and preferably will be a buffer solution. Preferably, the buffered pH is in the range of from 6.0 to 8.0. Suitable diluents include, e.g. phosphate citrate buffer. The concentration of the perfluoro alkyl acid in the buffer should be 0.1%-3%, preferably 0.5%. Suitable buffer solutions are customary in the art and do not require elucidation here.

The perfluoro alkyl acid can be added in a separate manner, but preferably is comprised in the sample diluent, preferably in the assay buffer.

The sample is contacted with an anti-25(OH)Vitamin D antibody The latter can be added to the sample, or the sample can be transferred to a reaction vial containing the binding protein.

Antibodies for vitamin D are known in the art, and are widely used in the existing immunoassays for vitamin D. These same antibodies, as well as other binding proteins, can be used in the present invention as well. E.g., in the place of an antibody for Vitamin D an antibody fragment can be used such as produced with phage display technology. Suitable antibodies can be monoclonal or polyclonal antibodies. They can be obtained in known manner, e.g. polyclonal goat anti-vitamin D, polyclonal rabbit anti-vitamin D, or any other suitable antibody for vitamin D as known in the art from application in immunoassays for vitamin D. Suitable antibodies are known, e.g. from the following references: Hollis, Clin. Chem 31/11, 1815-1819 (1985); Hollis, Clin. Chem 39/3, 529-533 (1993).

The antibodies as used are preferably immobilized. They are preferably used in a particulate form comprising solid carriers. Typically, the antibody is coated on a solid phase, e.g. on a microtiter plate. In a preferred embodiment, the antibodies are coated onto magnetic particles, which facilitates their separation in a magnetic field.

After addition of the antibody, the sample is allowed to incubate. The required time will depend on circumstances such as the concentration of the reagents, the type of binding protein, and conditions during incubation, e.g. shaking and temperature. Generally, the incubation time will be in a range of from 10 seconds to several hours, preferably 1 minute to 1 hour. For automated platforms, short incubation times (10 seconds to 10 minutes, preferably 30 seconds to 30 minutes) are preferred.

After the first incubation period, a conjugate of vitamin D with a functional label is added. Numerous labeled compounds are known that are capable of serving as competitive binding antigens in immunoassays for the determination of vitamin D. Typical labels are radiolabels, fluorescent labels, luminescent labels, biotin labels, gold labels, enzyme labels. Competitive binding assays are known to the skilled person, and do not require elucidation, notably since this part of the method of the invention can be carried out using any label known to be suitable for the determination of vitamin D. Labels that can be used are, inter alia, those disclosed in the foregoing references on existing vitamin D immunoassays.

With the label allowing measuring a concentration, as a result, the concentration of vitamin D in the sample is determined. It will be understood that the interpretation of the values measured, is determined by a calibration measurement, i.e. by the response—in the same assay—of calibrators.

The calibration for the assay of the invention can be done by providing calibrators comprising a predetermined concentration of 25-OH vitamin D. The concentration of Vitamin D in the calibrators is preferably determined using an LC-MS-MS method.

The invention, in another aspect, presents a product in the form of an immunoassay for the determination of 25-OH vitamin D in blood or blood components, wherein the assay makes use of a method according to any one of preceding embodiments. More particularly, such a product will be provided in the form of a kit for conducting the immunoassay. Such a kit may comprise the loose reagents involved, i.e. the antibody, the labeled vitamin D compound and the diluents/assay buffer. These reagents can be provided separately, and thus form a kit only upon their use in the assay of the invention. Preferably, the reagents are provided together, preferably packaged together, as one kit of parts. The kit optionally comprises a container for a sample of blood or blood components, but as is customary this may also be provided separately. Typically a kit comprises a binder immobilized on a solid phase and a separate conjugated vitamin D. Other kit components will depend, as is customary in the art, on the label chosen, as different labels may require different reagents.

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention will be illustrated with reference to the following, non-limiting Example and the accompanying non-limiting Figures.

EXAMPLE

Measurement of Vitamin D

The assay was performed using an automated platform. To 15 μl of sample 255 μl of sample diluent/assay buffer was added. An aliquot of 100 μl of the diluted sample was transferred to a second incubation well. A volume of 50 μl of magnetic particles coated with monoclonal antibody was added to the diluted sample and incubated for 45 minutes at 37° C. Subsequently 50 μl of a solution biotinylated Vitamin D was added and incubated for 7 minutes at 37° C. Then 50 μl of a solution streptaviclin-Acriclinium ester was added and again incubated for 7 minutes at 37° C. After magnetic separation of bound and free biotinylated Vitamin D, the bound acridinium ester was quantified.

Materials

Paramagnetic particles Magnetic particles (Invitrogen, M280 tosyl-activated, 2.8 μm) were coated with a polyclonal antibody against Mouse IgG (5 μg/mg of magnetic particles). The particles were coated on a roller at a concentration of 0.5 mg/ml in 0.01M PBS, 0.138M NaCl of pH 7.4 during 16 hours. Finally particles were blocked with 0.05M Tris/0.05% BSA containing 0.1% Proclin-950. The particles were coated during 16 hrs at 37° C. with a second layer of anti-Vitamin-D monoclonal antibody at a concentration of 0.4 μg/mg particles.

The sample diluent consisted of 0.1M TRIS buffer of pH 8.0 containing 0.05% BSA and 0.5% PFOA.

The conjugate (i.e. the labeled vitamin D compound) is a biotinylated Vitamin-D. The conjugate was presented at a concentration of 0.5 ng/ml in a 0.1M Tris buffer of pH 8.0 containing 0.05% Bovine Serum Albumin.

Protocol

To 15 μl of sample 255 μl of sample diluent/assay buffer was added. An aliquot of 100 μl of the diluted sample was transferred to a second incubation well. A volume of 50 μl of magnetic particles coated with monoclonal antibody was added to the diluted sample and incubated for 45 minutes at 37° C. Subsequently 50 μl of a solution biotinylated Vitamin D was added and incubated for 7 minutes at 37° C. Then 50 μl of a solution streptaviclin-Acriclinium ester was added and again incubated for 7 minutes at 37° C. After magnetic separation of bound and free biotinylated Vitamin D, the bound acridinium ester was quantified. A chemiluminescent signal was generated by addition of trigger reagent. The signal generated in the cuvette is inversely proportional to the concentration of 25 (OH)Vitamin D in the sample or calibrator. The concentration of 25(OH) vitamin D in the original sample can be calculated by comparing the signal of unknowns with the response of calibrators.

Results

In the table below, and in FIG. 1, a calibration curve is shown. 25(OH)Vitamin D3 calibrators were prepared in Vitamin D-free serum and ranged from 0-136 ng/ml.

Biotinylated 25(OH)Vitamin D is displaced to a level of 7% at 136 ng/ml.

Figure 2:
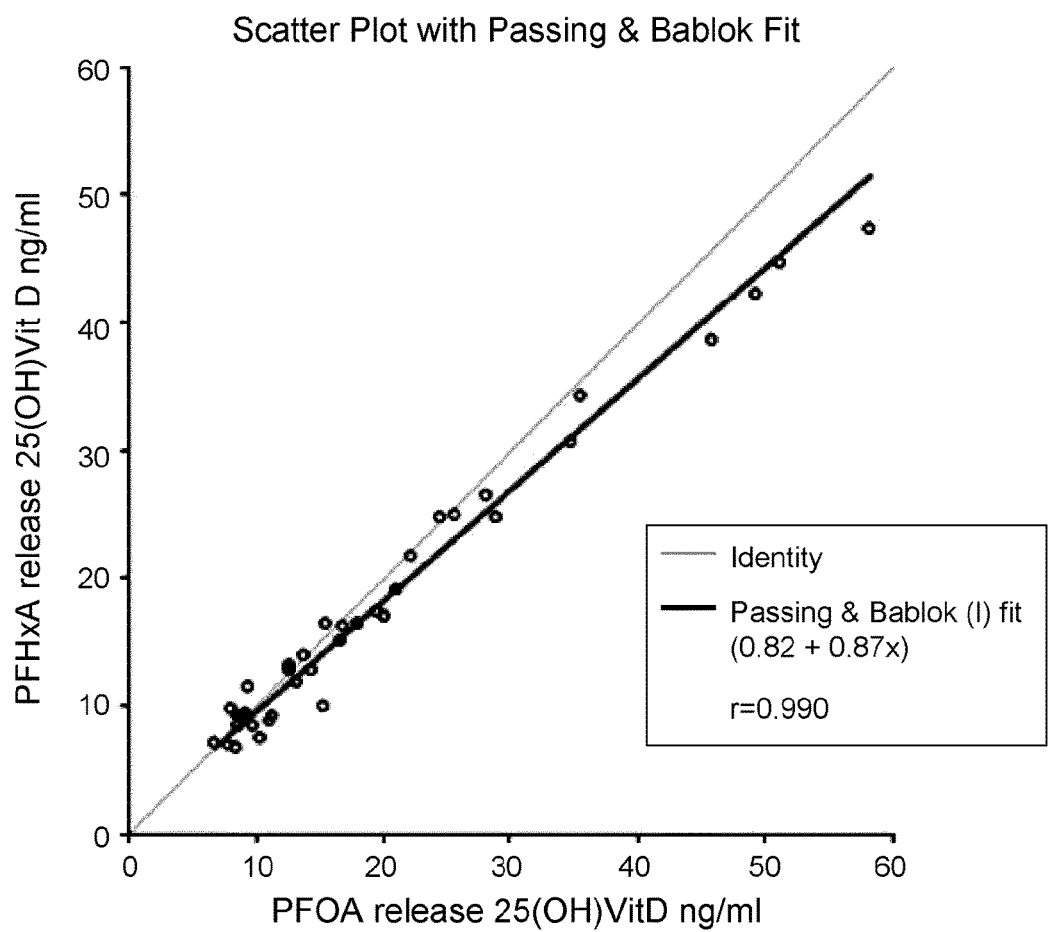
FIG. 2 presents a graph comparing results obtained with perfluorhexanoic (PFHxA) acid and with Perfluoroctanoic acid (PFOA) release.

A set of samples was measured using perfluoroctanoic acid release and with perfluorhexanoic acid release. Results correlate very well (r=0.990) indicating that both compounds can be used (FIG. 2).

TABLE

Table 1. 25(OH)Vitamin D calibration curve.

| Standard curve dose (ng/mL) | St 0 0 | St A 4.1 | St B 13.5 | St C 24.9 | St D 52.1 | St E 136 |
|---|---|---|---|---|---|---|
| RLU (1) | 733227 | 618731 | 432378 | 254588 | 105251 | 41737 |
| RLU (2) | 754974 | 637612 | 422703 | 228484 | 106879 | 41870 |
| RLU mean | 744101 | 628172 | 427541 | 241536 | 106065 | 41804 |
| RLU SD | 15377 | 13351 | 6841 | 18458 | 1151 | 94 |
| RLU % CV | 2.1% | 2.1% | 1.6% | 7.6% | 1.1% | 0.2% |
| Binding % | 100.0% | 84.4% | 57.5% | 32.5% | 14.3% | 5.6% |

The invention claimed is:

1. A method for assaying a sample of blood or blood components for 25-hydroxy vitamin D comprising
   providing a mixture by combining the sample with an aqueous buffer solution comprising from 0.5 to 3 wt. % of a perfluoro alkyl acid with carbon chain length of 4 to 12 or a salt thereof to release vitamin D from endogenous vitamin D binding protein and albumin,
   subjecting the mixture to incubation with an anti-vitamin D antibody;
   subjecting the mixture to incubation with a conjugate of vitamin D and a functional label for competitive binding to the anti-vitamin D antibody; and
   determining the concentration of total 25 hydroxy vitamin D in the sample by using a reference to a calibrator concentration for-25 hydroxy vitamin D.

2. A method of claim 1, wherein the perfluoro alkyl acid is selected from the group consisting of perfluoro hexanoic acid, perfluoro octanoic acid, and mixtures thereof.

3. A method of claim 1, wherein the sample is human serum or plasma.

4. A method of claim 1, wherein the anti-vitamin D antibody is coated on magnetic particles.

5. A method of claim 1, wherein the functional label is selected from the group consisting of radiolabels, fluorescent labels, luminescent labels, biotin labels, gold labels, enzyme labels.

6. A method of claim 1, wherein the perfluoro alkyl acid or the salt thereof is selected from the group consisting of perfluoro octanoic acid, perfluoro octanoic acid ammonium salt, and perfluoro octane sulfonate.

* * * * *